United States Patent
Ikami

(10) Patent No.: US 6,246,525 B1
(45) Date of Patent: *Jun. 12, 2001

(54) IMAGING DEVICE

(75) Inventor: Seishi Ikami, Kanagawa-ken (JP)

(73) Assignee: Fuji Photo Film Co., Ltd., Kanagawa-Ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/386,512

(22) Filed: Aug. 31, 1999

(30) Foreign Application Priority Data

Aug. 31, 1998 (JP) .................................................. 10-245790

(51) Int. Cl.[7] .................................................. G02B 27/10
(52) U.S. Cl. ............................................................ 359/619
(58) Field of Search ............................ 359/619; 348/292, 348/315; 257/226

(56) References Cited

U.S. PATENT DOCUMENTS

| | | | |
|---|---|---|---|
| 3,996,599 | * 12/1976 | King | 357/30 |
| 4,481,522 | * 11/1984 | Jastrzebski et al. | 357/24 |
| 5,417,494 | * 5/1995 | Kempa et al. | 374/5 |

* cited by examiner

*Primary Examiner*—Ricky Mack
(74) *Attorney, Agent, or Firm*—Sughrue, Mion, Zinn, Macpeak & Seas, PLLC

(57) ABSTRACT

In an imaging device for imaging the overall opposite surface of a sample carrier by an imaging means installed away from the sample carrier storing many imaging objects respectively in the direction of depth thereof, the effect of the parallax is eliminated by controlling an increase in cost.

A Fresnel lens 50 having refractive force for focusing light traveling in almost the same direction as the direction of depth of the wells 110 from the side of the plate 100 on the CCD 11 by a combination of the collection or camera lens 12 is provided between the micro-titer plate 100 storing the imaging objects 200 in each well 110 having a depth and the imaging means 10 for imaging fluorescence emitted from the wells 110 of the micro-titer plate 100.

4 Claims, 6 Drawing Sheets

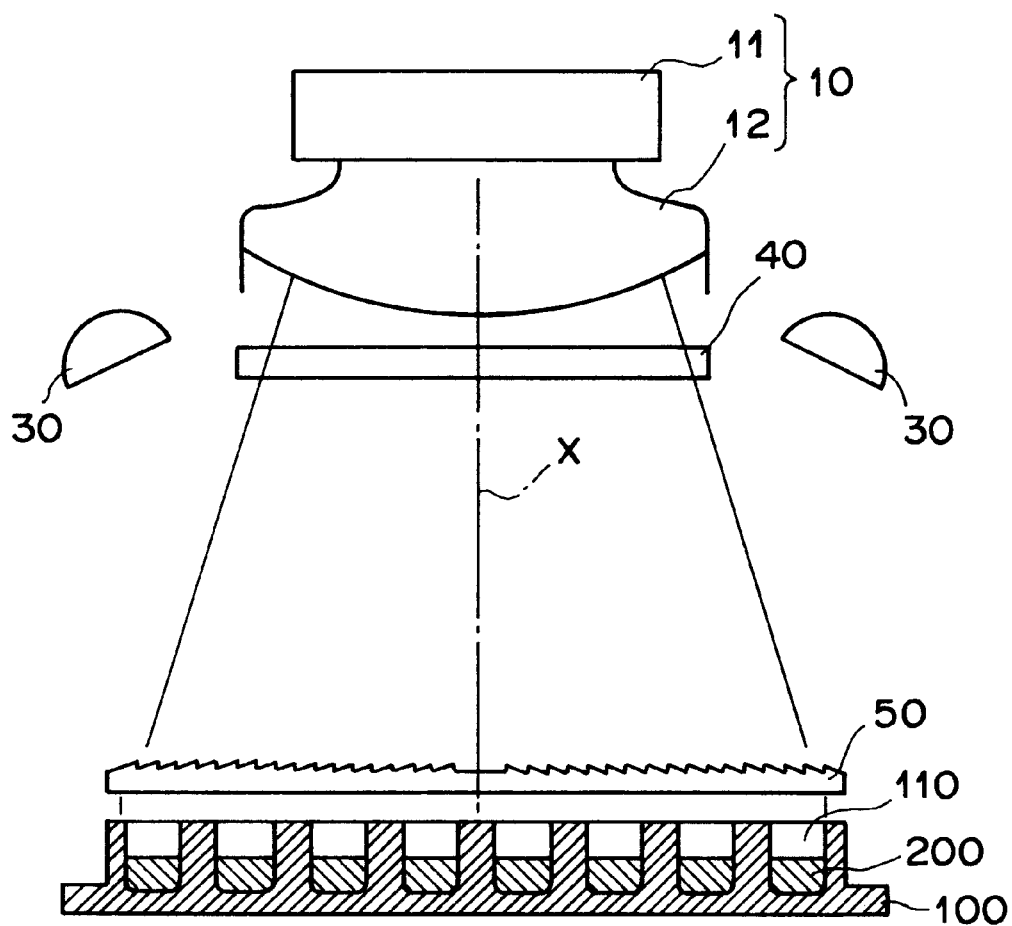
F I G . 1

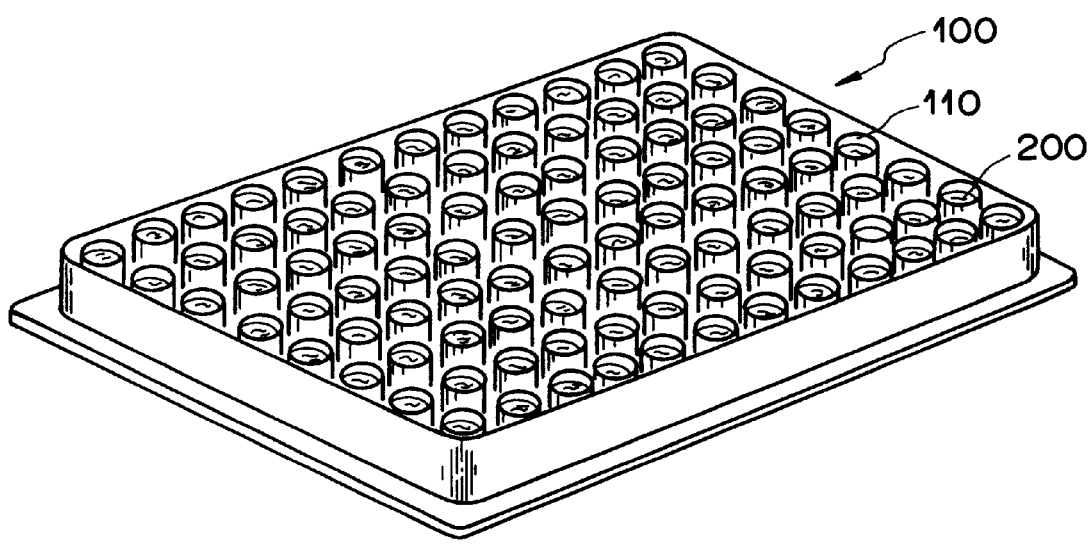
F I G . 2

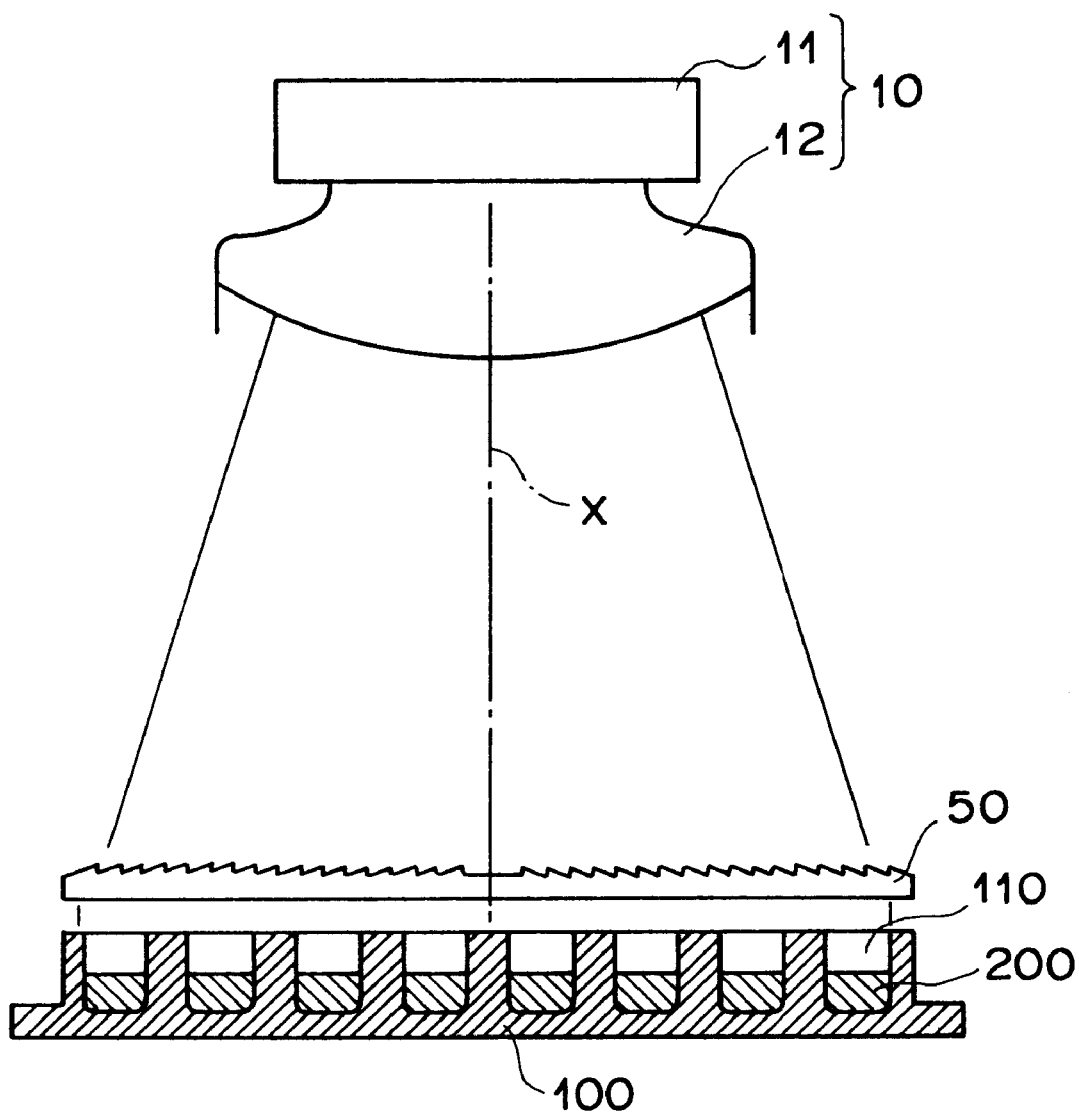
F I G. 3

— PRIOR ART —

IMAGING DEVICE

BACKGROUND OF THE INVENTION

1. Field of the Invention

The present invention relates to an imaging device and more particularly to an imaging device for imaging a sample carrier carrying an imaging object for measuring the density or color thereof or detecting the existence of light emission thereof.

2. Description of the Related Art

In the biochemistry and molecular biology fields, it is common practice to house imaging objects 200, which are samples, in each well 110 of a micro-titer plate 100 as shown in FIG. 2, and to set them in an imaging device having an imaging means 10 as shown in FIG. 5. The whole micro-titer plate 100 is imaged at one time, and the density and color of each imaging object 200 contained in each well 110, or the intensity of chemiluminescence or fluorescence, is measured on the basis of this picked-up image.

SUMMARY OF THE INVENTION

Meanwhile, as shown in the drawing, each well 110 of the micro-titer plate 100 has a predetermined depth in the thickness direction (depth direction) of the micro-titer plate 100 and on the other hand, the imaging means 10 of the imaging device is opposite to the plate 100 at a fixed image angle, so that with respect to the well 110 corresponding to the neighborhood of the optical axis X of the imaging means 10, optical information passing the optical path open through from the upper opening of the well 110 to the bottom is input into the imaging means 10 (see FIG. 6A). Therefore, the depth of the imaging object 200 stored in the well 110 becomes the optical path length in the imaging object 200 as it is and it can be measured accurately on the basis of the information input into this imaging means 10. However, with respect to the well 110 at the edge of the plate 100, optical information passing the optical path open through from the upper opening of the well 110 to the bottom is not input into the imaging means 10 due to parallax (see FIG. 6B). Therefore, with respect to the well 110 at the edge of the plate 100, a problem arises that it cannot be measured accurately on the basis of the information input into this imaging means 10.

This problem arises not only in the case of the aforementioned image determination using the micro-titer plate but also in the case of image determination of a sample carrier executing electrophoresis for an imaging object using gel with a certain thickness (for example, a thickness of 5 mm or more) and a Petridish for culture. In this case, the imaging object is immersed in the thickness direction of the gel, so that the immersed portion of the imaging object at the edge of the sample carrier is observed as a blot due to the parallax.

Therefore, to eliminate such a parallax effect, it may be considered to install a telecentric lens comprising a plurality of lenses and apertures between the imaging means and the sample carrier of the micro-titer plate.

However, the constitution of the telecentric lens is large-scale and expensive, so that an increase in cost of the imaging device to be used is inevitable.

The present invention was developed with the foregoing in view and is intended to provide an imaging device for eliminating the parallax effect by controlling an increase in cost and picking up an image for highly accurate image determination.

The imaging device of the present invention has a single lens arrangement for eliminating the parallax between the imaging means and an imaging object having a thickness. Namely, the imaging device of the present invention is an imaging device for imaging a sample carrier having many imaging objects having the depth in the same direction arranged on a plane perpendicular to the aforementioned direction, by an imaging means installed at a distance from the sample carrier, wherein a single lens having refractive force dependent upon the distance between the sample carrier and the imaging means is arranged at a location in the neighborhood of the sample carrier between the sample carrier and the imaging means, so that light traveling in almost the same direction as the aforementioned direction from the sample carrier focuses on the image forming surface of the imaging means.

In this case, as a single lens, it is desirable to use a Fresnel lens with a thin thickness which is low in cost.

As a sample carrier, a micro-titer plate or a gel with a thickness of about 3 mm or more can be used. Also, a Petridish for culture can be used.

According to the imaging device of the present invention, a single lens having refractive force dependent upon the distance between the sample carrier and the imaging means, which is arranged in the neighborhood of the sample carrier between the sample carrier and the imaging means so that light traveling in almost the same direction as the depth direction of an imaging object from the sample carrier focuses on the image forming surface of the imaging means, performs an action for forming an image of an imaging object existing at an infinite distance on the imaging means (eliminates the parallax). Therefore, even for an imaging object at the edge of the sample carrier, optical information passing the whole in the direction of the depth of the object can be imaged. Therefore, according to information input in the imaging means like this, accurate image determination can be carried out. Moreover, with respect to the aforementioned single lens, lenses sufficiently low in cost compared with a telecentric lens are in wide use and an increase in cost of the overall imaging device can be controlled. If a Fresnel lens is used as a single lens, the lens thickness can also be controlled, so that the degree of freedom with respect to arrangement in the device can also be enlarged.

BRIEF DESCRIPTION OF THE DRAWINGS

FIG. 1 is a drawing showing an embodiment of an imaging device of the present invention, FIG. 2 is a drawing showing an example of a micro-titer plate used in the imaging device shown in FIG. 1, FIG. 3 is a drawing showing another embodiment of an imaging device of the present invention.

DESCRIPTION OF THE PREFERRED EMBODIMENTS

Figure 4:
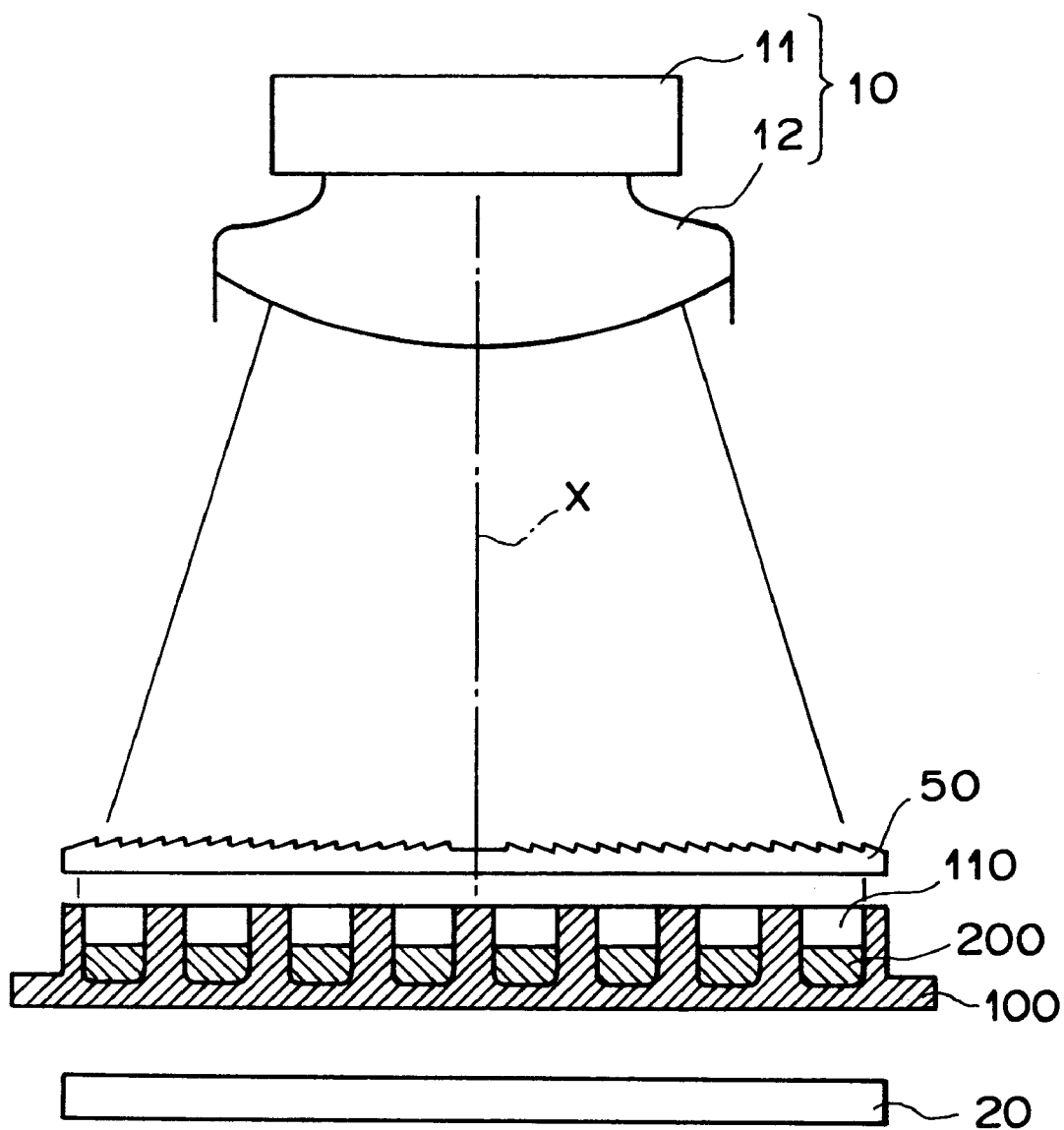
FIG. 4 is a drawing showing the second embodiment of an imaging device of the present invention.
Figure 5:
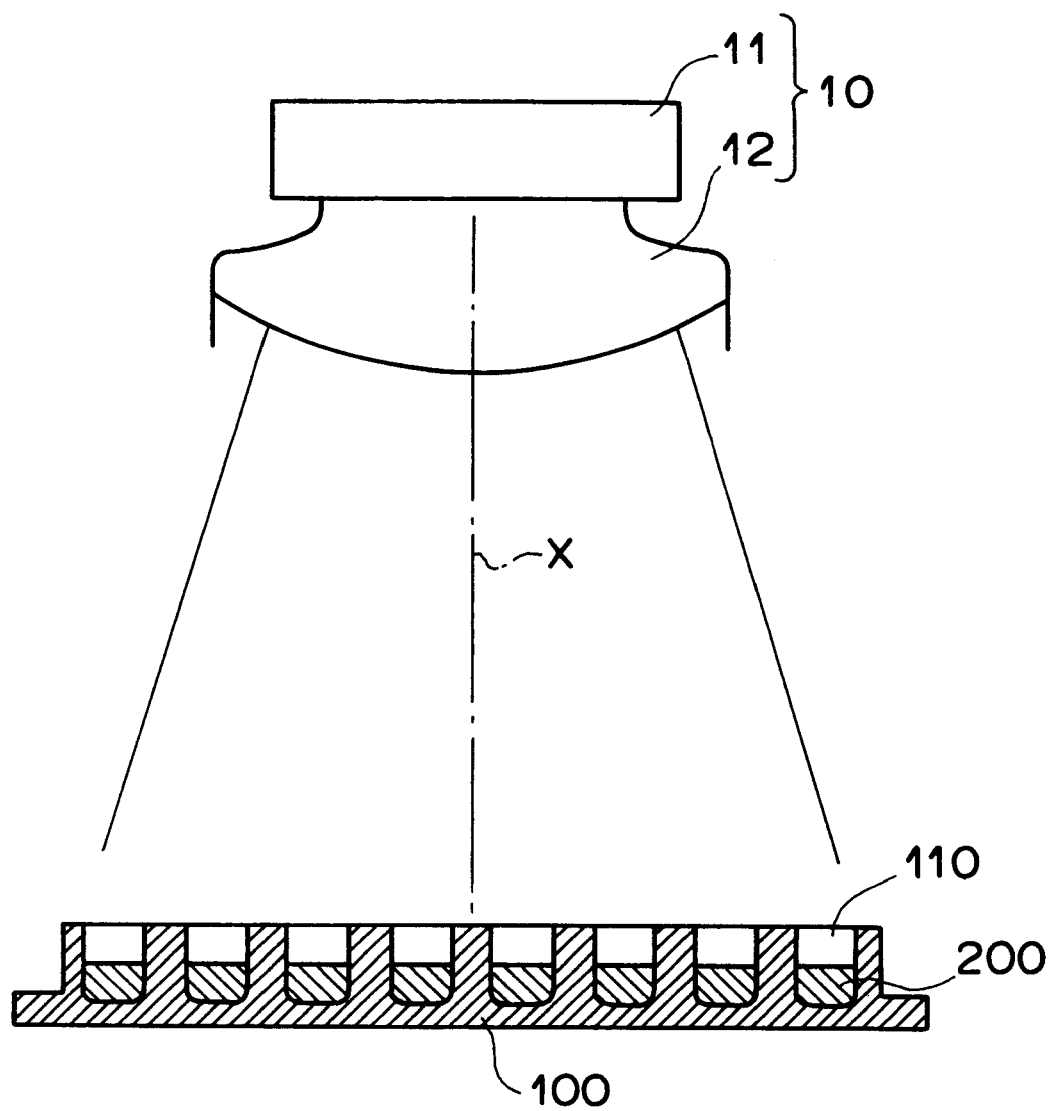
FIG. 5 is a drawing showing a conventional imaging device.
Figure 6A:
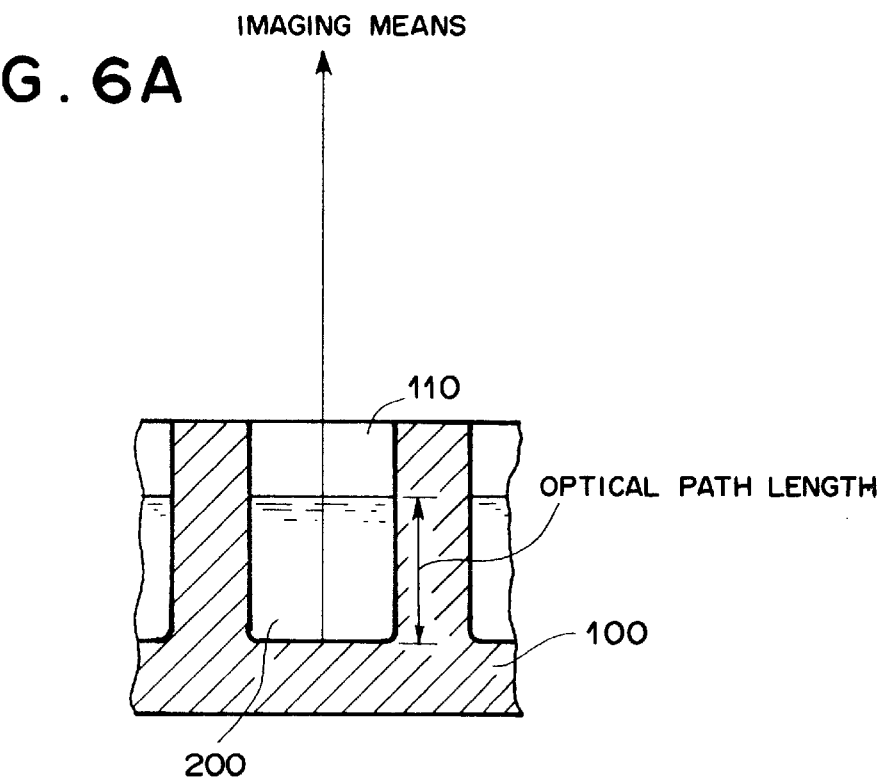
FIGS. 6A and 6B are drawings for explaining parallax.
Figure 6B:
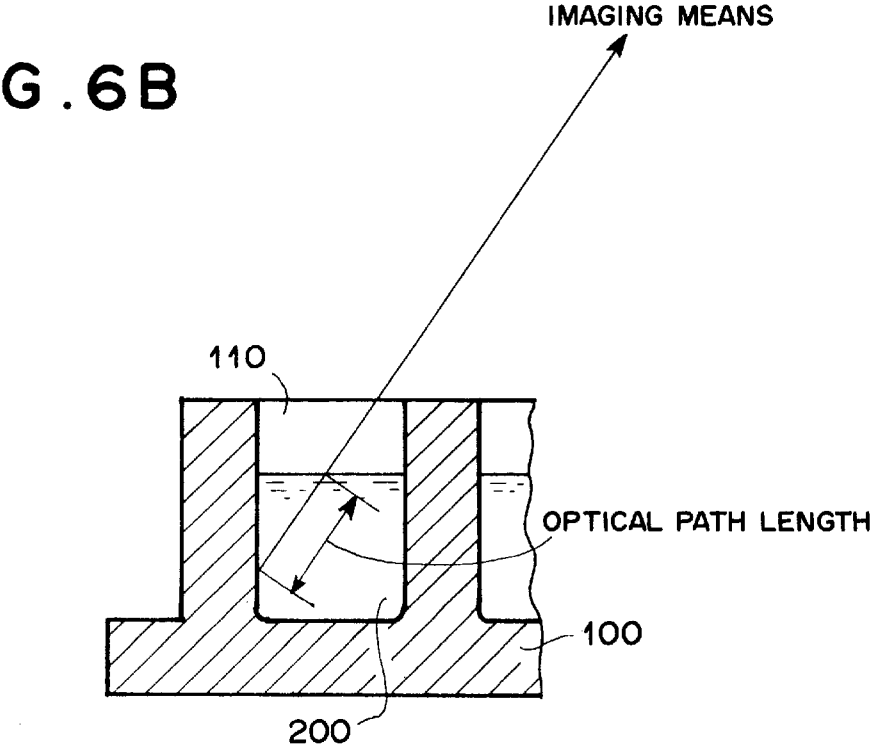

The embodiments of the imaging device of the present invention will be described hereunder with reference to the accompanying drawings.

FIG. 1 is a drawing showing an embodiment of the imaging device of the present invention and FIG. 2 is a perspective view showing a micro-titer plate used in FIG. 1.

In a micro-titer plate 100 shown in the drawing, there are formed many wells 110 formed of a transparent and colorless material which has a predetermined thickness, contains imaging objects 200, and has a depth in the thickness direction. The imaging objects 200 contained in the wells 110 are not always the same and, for example, there are imaging objects which are marked by a fluorescent material generating fluorescence upon receipt of predetermined exciting light or imaging objects which are not marked, and they are objects of fluorescence observation.

The imaging device shown in the drawing has a constitution that it has a incident light source 30 comprising an LED for irradiating exciting light with a center wave length of 470 nm for exciting the aforementioned fluorescent material and generating fluorescence toward the plate 100 from above the micro-titer plate 100 arranged at a predetermined location, imaging means 10 for imaging the overall surface of this plate 100 at one time which is arranged at a distance of about 300 mm from the plate 100, a fluorescence filter 40 for transmitting the aforementioned fluorescence which is installed in the neighborhood of the plate 100 between the imaging means 10 and the plate 100, and a Fresnel lens 50 in the neighborhood of the plate 100 between the imaging means 10 and the plate 100.

The imaging means 10 comprises a cooling CCD 11 where image pickup elements are arranged two-dimensionally and a collection or camera lens 12 having a focal length of 20 mm, and an image processing device not shown in the drawing is connected to the CCD 11.

In the micro-titer plate 100, the width in the lateral direction of the drawing is 130 mm, the depth of each well 110 is 11 mm, and the overall thickness is 14 mm. The Fresnel lens 50 is arranged only at a distance of 0 to 30 mm (when the distance is 0 mm, in contact with the top) from the top of the plate 100 and has refractive force for focusing light traveling in almost the same direction as the depth direction of the wells 110 from the side of the plate 100 on the CCD 11 by a combination of the exposure lens 12, with the focus length thereof being 290 mm.

The incident light source 30 is not limited to the aforementioned LED and the wave length of exciting light can be selected appropriately within the range from 400 to 900 nm according to the kind of a fluorescent material using excitation. Furthermore, instead of illumination for irradiating the overall surface of the plate 100 at one time, scanning light may be used.

Next, the operation of the imaging device of this embodiment will be explained.

Firstly, when the micro-titer plate 100 storing the imaging objects 200 which are objects of fluorescence observation in each well 110 is set in the predetermined location of the imaging device as shown in FIG. 1, and exciting light with a center wave length of 470 nm is irradiated onto the set plate 100 from the incident light source 30.

The exciting light irradiated onto the plate 100 irradiates the imaging objects 200 stored in each well 110 of the plate 100, and among the imaging objects 200, the imaging objects 200 marked by a fluorescent material by the predetermined preprocess are excited by the irradiated exciting light and emit fluorescence. On the other hand, the imaging objects 200 not marked by a fluorescent material will not emit fluorescence even if the exciting light is irradiated.

The fluorescence emitted from the wells 110 enters the Fresnel lens 50, is refracted by this Fresnel lens 50, passes through the fluorescence filter 40, is further refracted by the collection or camera lens 12, enters the CCD 11, and is detected photoelectrically. Reflected light of the exciting light from the surfaces of the plate 100 and the imaging object 200 is also emitted from each well 110, refracted by the Fresnel lens 50 in the same way as with fluorescence, and travels toward the imaging means 11. However, since it is cut out by the fluorescence filter 40, it will not enter the CCD 11.

As a result, in the CCD 11, only the image pickup elements corresponding to the wells 110 emitting fluorescence among all the wells 110 detect fluorescence. Since the parallax of the fluorescence entering the CCD 11 is eliminated by the Fresnel lens 50, even in the case of fluorescence emitted from the well 110 at the edge of the plate 100, the fluorescence reflected on the inner wall of the well 110 will not be erroneously detected as fluorescence emitted from the adjacent other wells 110.

As mentioned above, according to the imaging device of this embodiment, fluorescence emitted from the well 110 at the edge of the plate 100 can also be imaged in the same way as with observation of the well 110 from directly above, so that image information for performing accurate image determination with the parallax eliminated can be obtained.

The image information obtained by the imaging device of this embodiment is subjected to various image processes including shading correction by an image processing device not shown in the drawing and submitted for image determination.

Furthermore, the imaging device of this embodiment can image imaging objects 200 realizing chemiluminescence or bioluminescence without excitation by exciting light. When such imaging objects 200 are used as objects, it is desirable to use the constitution shown in FIG. 3 where the incident light source 30 for emitting exciting light and the fluorescence filter 40 are removed.

FIG. 4 is a drawing showing the second embodiment of the imaging device of the present invention. The imaging device shown in the drawing is an embodiment when the imaging objects 200 are objects to be subjected to image determination of the density and color.

Namely, in the imaging device of the embodiment shown in FIG. 1, the constitution is such that the transmitting light source 20 comprising a white light source for irradiating white light with a wave length of 400 to 700 nm from underneath the micro-titer plate 100 set in the imaging device is provided in place of the incident light source 30 and the fluorescence filter 40 is removed. When the image determination is to be performed on the basis of a specific color of the imaging objects 200, it is possible to arrange a filter for transmitting only the specific color.

The operation of the imaging device of this embodiment is basically the same as that of the imaging device of the embodiment shown in FIG. 1. Namely, in the embodiment shown in FIG. 1, light emitted from the imaging objects 200 is fluorescence excited by the downward illumination 30. However, in this embodiment, everything is the same except that light emitted from the imaging objects 200 is white light emitted from the transmitting light source 20 arranged under the plate 100 and transmitting through the imaging objects 200.

In the imaging device of each of the aforementioned embodiments, since the imaging objects are stored in the micro-titer plate having a thickness, they have a depth in the exposure direction. However, in addition to this, for example, by executing electrophoresis using an electrophoresis gel with a thickness of 3 mm or more, even when imaging objects having a depth in the direction of thickness (exposure direction) of the gel are to be imaged, the same effect can be obtained.

What is claimed is:

1. An imaging device for imaging a sample carrier, said sample carrier comprised of a plurality of objects to be imaged having a depth in a direction, said sample carrier being arranged on a plane perpendicular to said direction, said imaging device comprising an imaging means provided at a location away from said sample carrier, wherein a single lens having refractive force dependent upon a distance between said sample carrier and the imaging means and wherein said imaging means is arranged at a location between said sample carrier and said imaging means so that light traveling in substantially the same direction as said direction from said sample carrier is focused on an image forming surface of said imaging means.

2. An imaging device according to claim 1, wherein said single lens is a Fresnel lens.

3. An imaging device according to claim 1 or 2, wherein said sample carrier is a micro-titer plate.

4. An image device according to claim 1, further comprising an LED for irradiating exciting light and a fluorescent filter for fluorescence.

* * * * *